United States Patent
Cryer

[19]

[11] Patent Number: 6,129,707

[45] Date of Patent: Oct. 10, 2000

[54] INTRAVASCULAR CATHETER WITH EXPANDED DISTAL TIP

[75] Inventor: Brett W. Cryer, Lafayette, Calif.

[73] Assignee: Advanced Cardiovascular Systems, Inc., Santa Clara, Calif.

[21] Appl. No.: 09/010,380

[22] Filed: Jan. 21, 1998

[51] Int. Cl.[7] .................................................. A61M 29/00
[52] U.S. Cl. ....................... 604/96.01; 606/194
[58] Field of Search ................... 604/96, 97, 98, 604/103, 104, 507–509; 606/192, 194, 195

[56] References Cited

U.S. PATENT DOCUMENTS

| | | | |
|---|---|---|---|
| 4,362,150 | 12/1982 | Lombardi, Jr. et al. | 128/1 D |
| 4,423,725 | 1/1984 | Baran et al. | 128/207.15 |
| 4,531,943 | 7/1985 | Van Tassel et al. | 604/280 |
| 4,551,292 | 11/1985 | Fletcher et al. | 264/139 |
| 4,637,396 | 1/1987 | Cook | 128/344 |
| 4,642,101 | 2/1987 | Krolikowski et al. | 604/164 |
| 4,661,094 | 4/1987 | Simpson | 604/53 |
| 4,748,982 | 6/1988 | Horzewski et al. | 128/344 |
| 4,759,752 | 7/1988 | Stöber | 604/247 |
| 4,811,737 | 3/1989 | Rydell | 128/344 |
| 5,019,040 | 5/1991 | Itaoka et al. | 604/95 |
| 5,040,548 | 8/1991 | Yock | 128/898 |
| 5,192,295 | 3/1993 | Danforth et al. | 606/194 |
| 5,254,090 | 10/1993 | Lombardi et al. | 604/96 |
| 5,318,532 | 6/1994 | Franssica | 604/96 |
| 5,496,275 | 3/1996 | Sirhan et al. | 604/96 |
| 5,554,121 | 9/1996 | Ainsworth et al. | 604/96 |
| 5,769,819 | 6/1998 | Schwab et al. | 604/103 |

*Primary Examiner*—John D. Yasko
*Attorney, Agent, or Firm*—Heller Ehrman White & McCauliffe LLP

[57] ABSTRACT

An intravascular catheter of the invention has an improved distal tip with an expanded portion which has exterior transverse dimensions greater than an unexpanded portion proximally adjacent to the expanded portion. In one presently preferred embodiment the catheter has an inflatable balloon with a distal skirt which is secured to the unexpanded portion of the distal tip so as to provide an even exterior surface thereto.

7 Claims, 2 Drawing Sheets

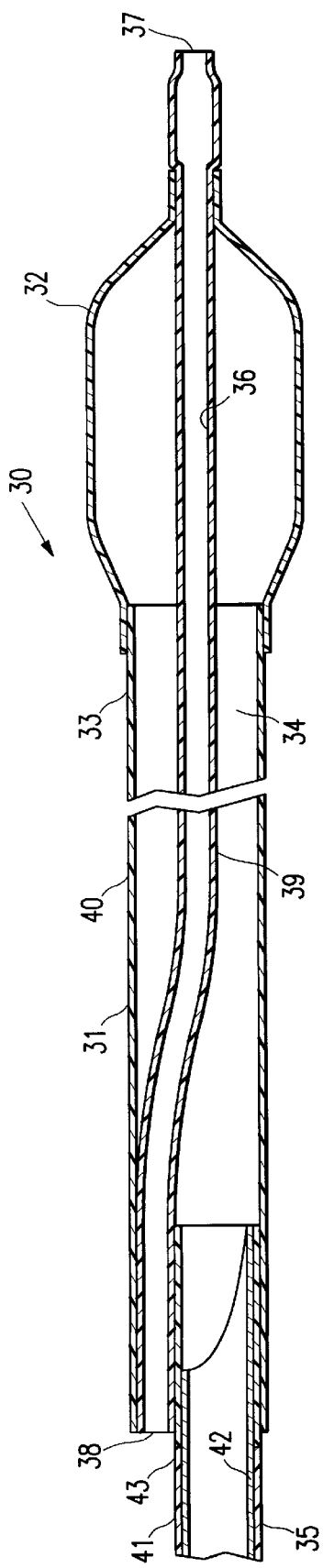
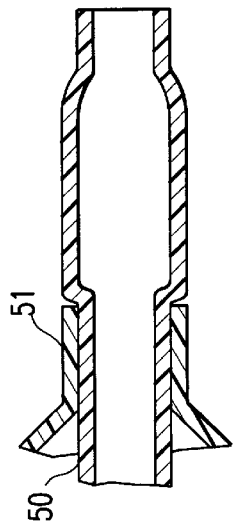
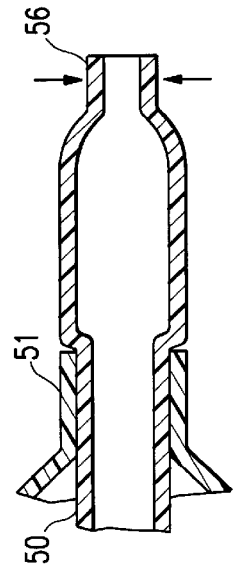
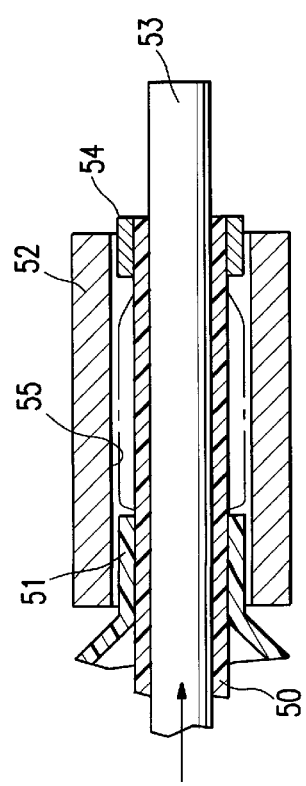

INTRAVASCULAR CATHETER WITH EXPANDED DISTAL TIP

BACKGROUND OF THE INVENTION

This invention generally relates to intravascular catheters, particularly catheters for use in percutaneous transluminal coronary angioplasty (PCTA) or stent delivery.

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures (generally 8–18 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

The distal tip of an intravascular catheter may be constructed to have non-traumatic characteristics to minimize damage when passing through a body lumen. A typical non-traumatic tip is formed from a short tubular member made of relatively soft polymeric material which is secured to the distal tip of the tubular distal extremity of the catheter. However, this construction does not always eliminate injury to the luminal lining. For example, the leading edge of the distal skirt of the balloon which extends radially outward can cause intimal injury even though it may be somewhat tapered. Moreover, securing a distal tip made from softer material or otherwise designed to collapse so as to avoid intimal injury, complicates the manufacturing procedure and increases its costs.

What has been needed and heretofore unavailable is a simple, inexpensive method for forming a nontraumatic distal tip. The present invention satisfies this and other needs.

SUMMARY OF THE INVENTION

This invention is directed to a distal tip construction for intraluminal catheters which has an improved non-traumatic characteristics and which is simple and inexpensive to produce.

The catheter of the invention generally has an elongated shaft with a proximal end, a distal end, a guidewire lumen extending through at least the distal portion of the catheter and a port in the distal end in fluid communication with the guidewire lumen. The elongated catheter has a tubular distal extremity which defines the guidewire lumen and which has an expanded portion with outer dimensions greater than a proximally adjacent unexpanded portion. Preferably, the tubular distal extremity tapers in the direction distal to the expanded portion to a smaller outer diameter at the distal end thereof which defines the port therein.

In one presently preferred embodiments of the invention, the catheter is a dilatation catheter having a balloon on a distal shaft section with an inner tubular member extending through and distal to the balloon which defines the guidewire lumen. The portion of the inner tubular member extending distal to the balloon is expanded in accordance with the present invention with the distal skirt of the balloon secured to an unexpanded portion of the inner tubular member proximally adjacent to the expanded portion. The distal skirt of the balloon is preferably sealingly bonded to the exterior of the unexpanded portion of the inner tubular member in a suitable manner such as by fusion or adhesive bonding. The expanded portion of the inner tubular member which extends distal to the distal skirt of the balloon preferably has outer dimensions which are essentially the same as or slightly larger than the outer dimensions of the distal skirt of the balloon so as to present a nontraumatic exterior to the interior of the body lumen in which the catheter is advanced.

The distal tubular extremity may be formed by placing it within a molding surface, such as a sheath, with interior dimensions the same as the desired dimensions of the expanded portion of the distal tubular extremity. The interior of the distal tubular extremity is then subjected to fluid pressure and the exterior to heat which causes the heated portion to soften or melt thereby expanding to the interior dimensions of the molding surface. The proximal portion of the distal tubular extremity, which is not to be expanded, may be supported exteriorly and not subjected to elevated temperatures so that it does not expand. The part of the distal tubular extremity distal to the expanded portion is likewise not expanded in a similar manner during the manufacturing procedure.

The expanded portion of the tubular distal extremity of the catheter ranges in length from about 0.1 to about 1.0 cm, preferably about 0.2 to about 0.5 cm. The overall length of the tubular distal extremity of the catheter which extends distal to the distal balloon skirt in the aforesaid presently preferred embodiment ranges from about 0.2 to about 1.5 cm, preferably about 0.3 to about 0.7 cm. The inner diameter or dimensions of the guidewire lumen extending through the expanded portion ranges from about 0.018 to about 0.035 inch (0.46–0.89 mm), preferably about 0.021 to about 0.025 inches (0.53–0.64 mm). The inner transverse dimensions of the guidewire lumen proximal to the expanded portion for a 3 mm balloon is about 0.013 to about 0.023 inches (0.33–0.58 mm), preferably about 0.016 to about 0.019 inch (0.41–0.48 mm) for a 0.014 inch (0.36 mm) guidewire. The guidewire lumen distal to the expanded portion is preferably tapered from the inner diameter of the expanded portion to transverse dimension slightly greater than the transverse dimensions of the guidewire to be passed therethrough. The wall thickness of the tubular distal extremity will vary depending upon the polymeric material from which the tubular member is made. The wall thickness of the expanded portion will usually be less than the unexpanded portion due to the expansion thereof by blowing unless the wall thickness of the portion to be expanded is initially greater than the portion which is not to be expanded.

The present invention provides an improved non-traumatic distal tip for intravascular catheters, which has gradual distal transitions in both profile and stiffness. This is particularly advantageous in balloon dilatation catheters where the distal skirt of the balloon can be secured to the unexpanded portion of the distal tubular extremity of the catheter proximal to the expanded portion so as to present a distal tip with a smooth, uniform exterior.

These and other advantages of the invention will become more apparent from the following detailed description of the invention when taken in conjunction with the accompanying exemplary drawings.

BRIEF DESCRIPTION OF THE DRAWINGS

FIG. 3 is an elevational schematic view of the distal portion of another alternative embodiment of the invention wherein the catheter is of a rapid exchange type dilatation catheter.

FIG. 4 schematically illustrates the forming of the distal tubular extremity of the catheter shown in FIG. 1.

FIG. 5 illustrates the distal tip as formed in FIG. 4.

FIG. 6 illustrates the distal tip as in FIG. 5 with the additional step of necking the most distal portion.

DETAILED DESCRIPTION OF THE INVENTION

Figure 1:
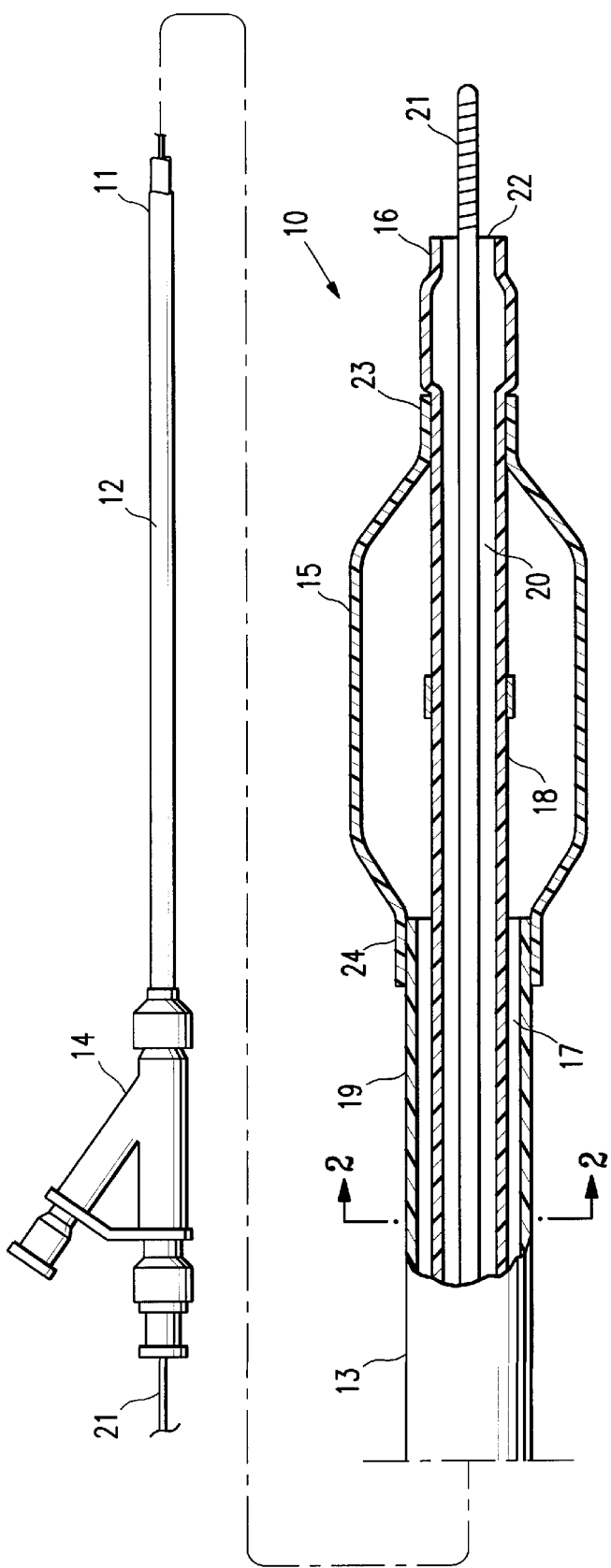
FIG. 1 is an elevational schematic view, partially in section, of a dilatation catheter embodying features of the invention.
Figure 2:
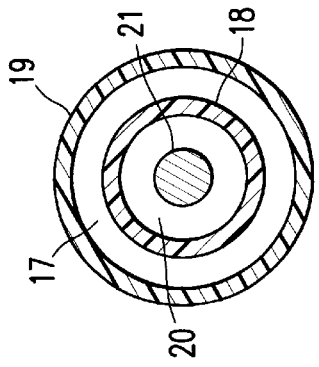
FIG. 2 is a transverse cross-sectional view of the catheter shown in FIG. 1 taken along the lines 2—2.

Reference is made to FIGS. 1 and 2 which illustrate a balloon dilatation catheter 10 embodying features of the invention. Catheter 10 has an elongated shaft 11 with proximal and distal shaft sections 12 and 13, an adapter 14 on the proximal end of the shaft and a dilatation balloon 15 on the distal shaft section spaced proximal to the distal end 16. An inflation lumen 17 extends between the proximal end of shaft 11 and a location spaced proximal to the distal end 16 and is in fluid communication with the interior of the dilatation balloon 15. The catheter shaft 11 is provided with an inner tubular member 18 and an outer tubular member or jacket 19 of suitable polymeric material. A guidewire receiving lumen 20 extends within both the proximal and distal shaft sections 12 and 13. In the distal shaft section 13, the guidewire receiving lumen 20 is defined at least in part by the inner tubular member 18. Guidewire 21 is slidably disposed within the inner lumen 20 and extends out the port 22 in the distal end 16.

The balloon 15 has a distal skirt 23 which is secured to an unexpanded portion of the distal extremity of the inner tubular member 18 and a proximal skirt 24 which is secured to distal end of the outer tubular member 19. The distal portion of the inner tubular member 18 which extends beyond the distal end of the distal skirt 23 is expanded so as to have an outer diameter or dimension approximately the same as or slightly greater than the outer diameter or dimension of the distal skirt.

The outer tubular member or jacket 19 may be formed of suitable polymeric material such as high density polyethylene, a polyester such as Hytrel® (trademark of DuPont), polyetheretherketone (PEEK) or a variety other polymeric materials. For other suitable polymeric materials, see the discussions of high modulus polymeric materials for catheter shafts found in U.S. Pat. No. 5,554,121 which issued on Sep. 26, 1996 and which is incorporated herein by reference in its entirety. The balloon 15 may be formed of homopolymers or blends of nylon, polyethylene terephthalate (PET), polyethylene, ionomers such as Surlyn® (DuPont). The balloon material is usually compatible with the material of the inner tubular member 18 so that a fusion bond can be easily formed between the distal skirt of the balloon and the inner tubular member The first inner tubular member 18 may be formed of the same material as the outer tubular member 19 or a lubricious material such a fluoropolymer or a hydrophilic material, e.g. the ethylene ethyl acrylate copolymer described in copending application Ser. No. 08/279,239, filed on Jul. 22, 1994, which is incorporated herein by reference in entirety. The low friction surface of the first inner tubular member 18 defining the guidewire receiving lumen 20 facilitates the advancement of a guidewire 21 within the guidewire receiving lumen. The inner tubular member 18 may be a coextruded member so that the exterior is compatible for fusion bonding to the balloon skirt and the interior has a lubricious surface. The inner tubular member 18 typically has an outer diameter of about 0.025 inch (0.6 mm) an inner diameter of about 0.018 inch (0.46 mm).

FIG. 3 schematically illustrates another embodiment of the invention wherein the dilatation catheter 30 is provided with rapid exchange characteristics such as described in U.S. Pat. No. 5,040, (Yock), U.S. Pat. No. 4,748,982 (Horzewski et al), U.S. Pat. No. 5,496,275 (Sirhan et al) and U.S. application Ser. No. 08/183,574, filed on Jan. 18, 1994 which have been incorporated herein. The catheter 30 generally has an elongated catheter shaft 31 and an inflatable dilatation balloon 32 on the distal shaft section 33. An inflation lumen 34 extends within the proximal shaft section 35 and the distal shaft section 33 to a location spaced proximal to the distal end of the catheter shaft 31 and is in fluid communication with the interior of the balloon 32. A guidewire lumen 36 extends from the distal port 37 in the distal end of the catheter shaft 31 to a proximal port 38 spaced proximal, about 7 to about 45 cm, preferably about 15 to about 35 cm, from the distal end of the catheter shaft.

The distal shaft section 33 has a concentric construction with an inner tubular member 39 which defines the guidewire lumen 36 and an outer tubular member 40 which is disposed about the inner tubular member and which defines the inflation lumen 34 between the inner and outer tubular member. The proximal portion of the distal shaft section 33 is generally formed with the proximal extremity of the outer tubular member 40 which is disposed about and secured to the proximal extremity of the inner tubular member 39 and the distal extremity of the tubular member 41 which forms the proximal shaft section 35. The proximal shaft section 35 is preferably formed of a hypotube 42 and an outer polymeric jacket 43. The distal extremity of the hypotube 42 may be tapered as shown to facilitate entry into the interior of the interior of the outer tubular member 40 and to provide a flexible joint between the proximal and distal shaft sections. If desired the first inner tubular member 40 and the outer tubular member 42 may be bonded together and a slit (not shown) may be provided through the bonded portions of said walls to facilitate separation of the catheter 30 and a guidewire (not shown) in the manner described in U.S. Pat. No. 4,748,982 (Horzewski et al) which has been incorporated herein by reference. One or more proximal perfusion ports (not shown) can be provided in the distal section of the catheter shaft 31 proximal to the balloon 32 which are in fluid communication with the guidewire lumen 36 and one or more distal perfusion ports (not shown) can be provided in the first inner tubular member distal to the balloon which are also in fluid communication with the guidewire lumen defined by the inner tubular member to facilitate the perfusion of oxygenated blood distal to the catheter when the balloon is inflated to dilate a lesion within the arterial passageway. Such perfusion ports are disclosed in U.S. patent application Ser. No. 08/484,267, filed on Jun. 7, 1995, which is incorporated herein by reference in its entirety.

FIG. 4 schematically illustrates a method of forming the tubular distal extremity of the invention where the tubular member is indicated by reference number 50, the distal skirt of a balloon by reference number 51 and a heating platen and molding member by reference number 52. A mandrel 53 is fitted into the distal end of the inner tubular member 50 and a band or collar 54 is bound about the exterior of the distal end of the inner tubular member 50 so as to seal the distal end thereof. The interior of the tubular member 50 is subjected to high pressure fluid and the portion to be expanded to elevated temperature which causes the heated portion to expand outwardly, as shown in phantom, to the molding surface 55. The most distal portion of the inner tubular member is not heated or expanded and so forms a smooth taper from the expanded portion to the smaller portion. The final distal extremity is shown in FIG. 5. As shown in FIG. 6, the unexpanded part 56 forming the most distal portion may be necked prior to or after the expansion to form a smaller diameter port. If the materials of the tubular member 50 and the distal skirt 51 of the balloon are compatible, the distal skirt of the balloon can be bonded to the tubular member at the same time as the more distal portion of the inner tubular member is being expanded.

To the extent not described herein or in any of the U.S. patents or patent applications which have been incorporated herein by reference, the dimensions, structural details and materials of construction may follow conventional practice for intravascular catheters such as balloon dilatation catheters used in angioplasty procedures or for stent delivery and implacement.

Various changes and modification may be made to the present invention without departing from the scope of the invention. For example, the distal shaft section of the catheter proximal to the balloon could be of an extruded dual lumen construction.

What is claimed is:

1. A balloon catheter comprising:

a) an elongated catheter shaft having proximal and distal ends, a port in the distal end, a guidewire lumen extending at least within a distal portion of the catheter shaft to and in fluid communication with the port in the distal end and an inflation lumen extending through the catheter shaft to a location spaced proximal to the distal end;

b) a balloon on the distal portion of the catheter shaft having an interior chamber which is in fluid communication with the inflation lumen and a distal skirt;

c) a inner tubular member extending through the interior chamber of the balloon, having the distal balloon skirt secured to the exterior of the inner tubular member and having an expanded portion extending beyond the distal skirt of the balloon which has outer transverse dimensions greater than outer dimensions of the distal skirt of the balloon.

2. The balloon catheter of claim 1 wherein the inner tubular member has a portion distal to the expanded section which tapers to outer transverse dimensions smaller than the outer transverse dimensions of the expanded section.

3. The balloon catheter of claim 2 wherein the tapered portion distal to the expanded portion has transverse dimensions smaller than transverse dimensions of the unexpanded portion proximal to the expanded portion.

4. The balloon catheter of claim 1 wherein the expanded section of the distal tubular extremity has a length of about 0.1 to about 1 cm.

5. The balloon catheter of claim 1 wherein the expanded section of the distal tubular extremity has a length of about 0.2 to about 0.5 cm.

6. The balloon catheter of claim 1 wherein a portion of the distal tubular extremity distal to the expanded portion is unexpanded.

7. The balloon catheter of claim 1 wherein the length of the distal tubular extremity including the expanded portion and the distal unexpanded portion is about 0.2 to about 1.3 cm.

* * * * *